US011585799B2

United States Patent
Bakhtari (10) Patent No.: US 11,585,799 B2
(45) Date of Patent: Feb. 21, 2023

(54) SYSTEM FOR MONITORING THE PROBABILITY OF VIRAL DISEASE TRANSMISSION

(71) Applicant: IDES Canada Inc., Stouffville (CA)

(72) Inventor: Ardevan Bakhtari, Stouffville (CA)

( * ) Notice: Subject to any disclaimer, the term of this patent is extended or adjusted under 35 U.S.C. 154(b) by 31 days.

(21) Appl. No.: 17/318,836

(22) Filed: May 12, 2021

(65) Prior Publication Data

US 2022/0365053 A1  Nov. 17, 2022

(51) Int. Cl.
| | |
|---|---|
| G01N 33/00 | (2006.01) |
| G01N 33/497 | (2006.01) |
| F24F 11/64 | (2018.01) |
| F24F 11/76 | (2018.01) |
| F24F 11/88 | (2018.01) |
| F24F 110/70 | (2018.01) |
| F24F 120/10 | (2018.01) |
| F24F 110/10 | (2018.01) |
| F24F 110/20 | (2018.01) |
| F24F 110/64 | (2018.01) |

(52) U.S. Cl.
CPC .......... *G01N 33/0065* (2013.01); *F24F 11/64* (2018.01); *F24F 11/76* (2018.01); *F24F 11/88* (2018.01); *G01N 33/0031* (2013.01); *G01N 33/0075* (2013.01); *G01N 33/497* (2013.01); F24F 2110/10 (2018.01); F24F 2110/20 (2018.01); F24F 2110/64 (2018.01); F24F 2110/70 (2018.01); F24F 2120/10 (2018.01)

(58) Field of Classification Search
CPC .......... G01N 33/0065; G01N 33/0031; G01N 33/0075; G01N 33/497; F24F 11/64; F24F 11/76; F24F 11/88; F24F 2110/10; F24F 2110/20; F24F 2110/64; F24F 2110/70; F24F 2120/10

See application file for complete search history.

(56) References Cited

U.S. PATENT DOCUMENTS

| | | | |
|---|---|---|---|
| 11,000,613 B1* | 5/2021 | Kellogg, Jr. | F24F 11/75 |
| 11,056,242 B1* | 7/2021 | Jain | G16H 10/60 |
| 11,127,506 B1* | 9/2021 | Jain | H04W 4/021 |
| 2019/0209806 A1* | 7/2019 | Allen | A61M 21/0094 |
| 2020/0348038 A1* | 11/2020 | Risbeck | F24F 11/70 |
| 2021/0011443 A1* | 1/2021 | McNamara | F24F 11/0001 |
| 2021/0018210 A1* | 1/2021 | Nasis | G01N 33/0032 |
| 2021/0048206 A1* | 2/2021 | Forzani | F24F 11/77 |
| 2021/0381861 A1* | 12/2021 | Brown | G05D 27/02 |
| 2021/0390807 A1* | 12/2021 | Chaurasia | G07C 9/27 |
| 2021/0390812 A1* | 12/2021 | Chaurasia | G01J 5/0025 |
| 2021/0391089 A1* | 12/2021 | Eswara | G16H 40/20 |
| 2021/0398690 A1* | 12/2021 | Gibson | G16H 40/20 |
| 2021/0405173 A1* | 12/2021 | Elias | G06N 20/00 |
| 2022/0010996 A1* | 1/2022 | Carrieri | F24F 11/63 |
| 2022/0054687 A1* | 2/2022 | Forzani | A61L 2/22 |
| 2022/0082280 A1* | 3/2022 | Douglas | F24F 3/16 |

(Continued)

*Primary Examiner* — Ramesh B Patel
(74) *Attorney, Agent, or Firm* — Nasser Ashgriz; UIPatent Corp (57) ABSTRACT

A system for assessing an indoor space for favorable conditions for the transmission of a viral particle is disclosed. A set of sensors measure a set of environmental parameters, and a processor is configured to combine the measured set of environmental parameters into a single scale of numerical or descriptive value representing the favorability of viral transmission in the indoor space.

8 Claims, 9 Drawing Sheets

(56) References Cited

U.S. PATENT DOCUMENTS

| | | | |
|---|---|---|---|
| 2022/0102012 A1* | 3/2022 | Son | G16H 10/40 |
| 2022/0105220 A1* | 4/2022 | Ufkes | A61L 2/26 |
| 2022/0136730 A1* | 5/2022 | Schoch | F24F 11/49 |
| | | | 700/276 |
| 2022/0178574 A1* | 6/2022 | Dong | F24F 11/74 |

* cited by examiner

SYSTEM FOR MONITORING THE PROBABILITY OF VIRAL DISEASE TRANSMISSION

FIELD OF THE INVENTION

The present invention relates generally to environmental monitoring, and especially to determination of the probability of viral transmission in an enclosed space.

BACKGROUND OF THE INVENTION

Viral disease transmission mostly occurs in indoor spaces where a group of people assemble. This is especially true of airborne viruses such as COVID-19 and SARS. Several factors aid in the transmission of the virus from one individual to the next when they are present in the same enclosed air space. These factors include occupancy to air volume ratio, occupancy to fresh air intake, relative humidity, temperature, and fine particulate concentration in the air. Public and private establishments can significantly reduce the chances of viral transmission among the occupants by optimizing these parameters through better building and HVAC design as well as control of occupancy loading.

To be able to fully assess the quality of an indoor space for viral transmission a single numerical value, herein referred to as Viral Transmission Score (VTS), is required that would consider not only each of the above-mentioned factors but also their combined affect. The single numerical number would be corelated to the probability of transmission of airborne viruses between occupants if any occupants were contagious. This viral transmission score can aid in: determination of occupancy load in real-time; providing alarm for highly contagious environments; and, allowing regulators to set limits to force establishments to improve HVAC/building design.

There are currently no instruments on the market that will provide a viral transmission score or equivalent. All previously developed systems focus only on detection of an infectious person or a specific virus within a monitored environment. This does not consider any of the parameters that would aid in the transmission of the infection from one person to the next within the monitored space.

By monitoring for contagious persons or an airborne virus, the current available systems are a reactive solution that will not aid in better building design or be compatible with a regulatory framework. These systems are also complicated and impractical to be widely used.

The present invention uses a network of electronic sensors to monitor parameters that can be used to determine the key factors that would affect the viral transmission score of an indoor space. These parameters such as occupancy load, fresh air intake rate, and particulate filtration, can be monitored directly or indirectly using proxy parameters. These proxy parameters may include but are not limited to carbon dioxide (CO2) and ultrafine particulate matter. The proposed system would collect continuous data on the measured parameters and fuse the data to create the single numerical value to represent the viral transmission score.

SUMMARY OF THE INVENTION

The present invention is a method for assessing an indoor space for favorable conditions of viral transmission comprising. A single or network of sensors measures parameters such as environmental conditions, occupancy load, fresh air rate and enclosed air space. An algorithm that combines measured parameters into a single scale of numerical or descriptive value representing the favorability of viral transmission in the monitored space.

The sensor network comprise of a temperature sensor to assess the viability of the virus in ambient environment, relative humidity sensor to assess the duration that the viral particle remains airborne, particulate sensor providing size and density concentration of particles in the ambient air utilized by virus to remain airborne and enter an occupant's lungs, carbon dioxide sensor to: assess the occupancy load to fresh air intake ratio, and estimate accumulation of viral load in the indoor air based on prior occupancy and fresh air intake.

The system may further comprise one or more of the following sensors: (a) Water droplet sensor used to determine ratio of particles comprise of water droplet. This can be achieved through use of dual particle counters which one has a preheated sample inlet. (b) An occupancy sensor such as camera, person counter at the entrance, or infrared sensor. (c) Air flow sensor directly on the HVAC system to determine filtration rate of indoor air volume or fresh air intake rate.

The algorithm provides higher score for spaces with higher occupancy to fresh air intake ratio, higher score for spaces with possible accumulated viral load from prior occupancy, higher score for spaces with higher particulate count, higher score for spaces with particulate distribution favoring smaller particulate sizes, higher score for spaces with lower relative humidity, lower score for spaces with increased temperature lowering infection efficiency.

In this method a single score is determined using a linear or non-linear combination of the effects of the measured parameters. A single parameter is used as the primary indicator and other parameters are used to amplify or suppress this parameter to determine the final viral transmission score.

The objective of the Viral Transmission Score (VTS) is to provide a singular metric assessing the conditions of an indoor environment for transmission of infectious diseases among the occupants. This singular metric will encompass factors that will affect the probability of viral transmission including occupancy rate, fresh air intake, temperature, humidity, and particulate concentration. This will allow: Governmental regulators to set VTS limits that would keep occupants safer that simple occupancy limits. Rapid inspect and continuous monitoring of an indoor space to identify deficiencies in HVAC system, occupancy control, and other systems that would affect the safety of the occupants in terms of disease transmission. Building engineers to take viral transmission into account when designing a new space to ensure occupant safety.

The second objective is to provide continuous reading of the Viral Transmission score using electronic sensors for remote monitoring of the key related factors. The automated system is a cost effective and easy to implement continuous monitoring system that will provide: Variation in viral transmission score as key factors such as occupancy rate fluctuations over time.

Alarms that can be used to trigger maintenance tasks, change in occupancy policy, and/or evacuation.

Control signal to modify functionality of HVAC system to increase fresh air intake, fine particulate filtration, and/or increase in humidity or temperature to reduce probability of viral transmission.

Regulatory reporting to demonstrate compliance with legal and regulatory requirements.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF PREFERRED EMBODIMENTS

Figure 1:
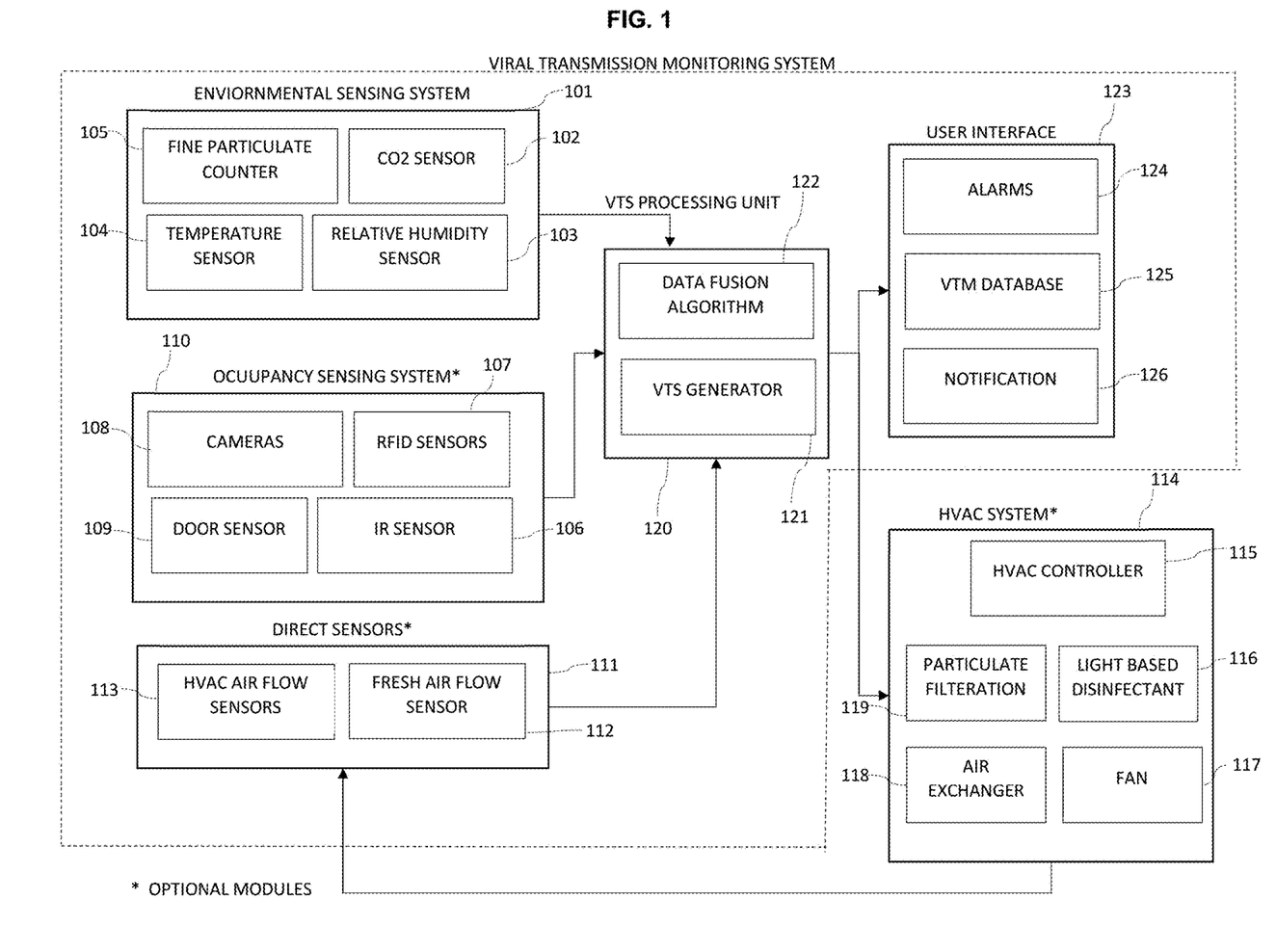
FIG. 1 shows one embodiment of the Viral Transmission Monitoring System.

The Viral Transmission Monitoring System 100, illustrated in FIG. 1 consists of environmental sensing system 101, a VTS processing unit 122, and user interface 123, with optional occupancy sensing system 110.

The environmental sensing system 101, comprises of (but not limited to) carbon dioxide sensors 102, fine particulate sensors 105 capable of measuring particulate mass concentration in the ambient air, temperature sensors 104, and relative humidity sensors 103.

The occupancy sensing system 110, may use cameras 108 and an image processing program to count the number of occupants in the enclosed space. Alternatively, an RFID sensor 107 can be used to count the number of occupants given that each occupant has an RFID transponder for example in the form of an access card or pre-installed on each shopping cart. The number of occupants can also be determined through a door sensor 109 or an IR sensor 106. Other technologies can also be used to provide either count of the number of occupants or a simple binary occupied/not occupied status.

The Viral Transmission Monitoring system may also consider readings from direct sensors 111 of a building Heating Ventilation and Air Conditioning system 114 and provide it with commands to reduce the probability of viral transmission in the enclosed space. Direct sensors may include HVAC air flow sensor 113 and fresh air flow sensors 112. The HVAC controller 115, may activate air circulation fan 117 to filter the air using a particulate filter 119 and or light-based disinfectant 116. An air exchanger 118 may also be used to introduce fresh air into the system.

Exceedance in probability of viral transmission can trigger alarms 124 and notifications 125 through the user interface 123. Historic data can be accessed by the user as all readings are recorded in a database 125.

Figure 2:
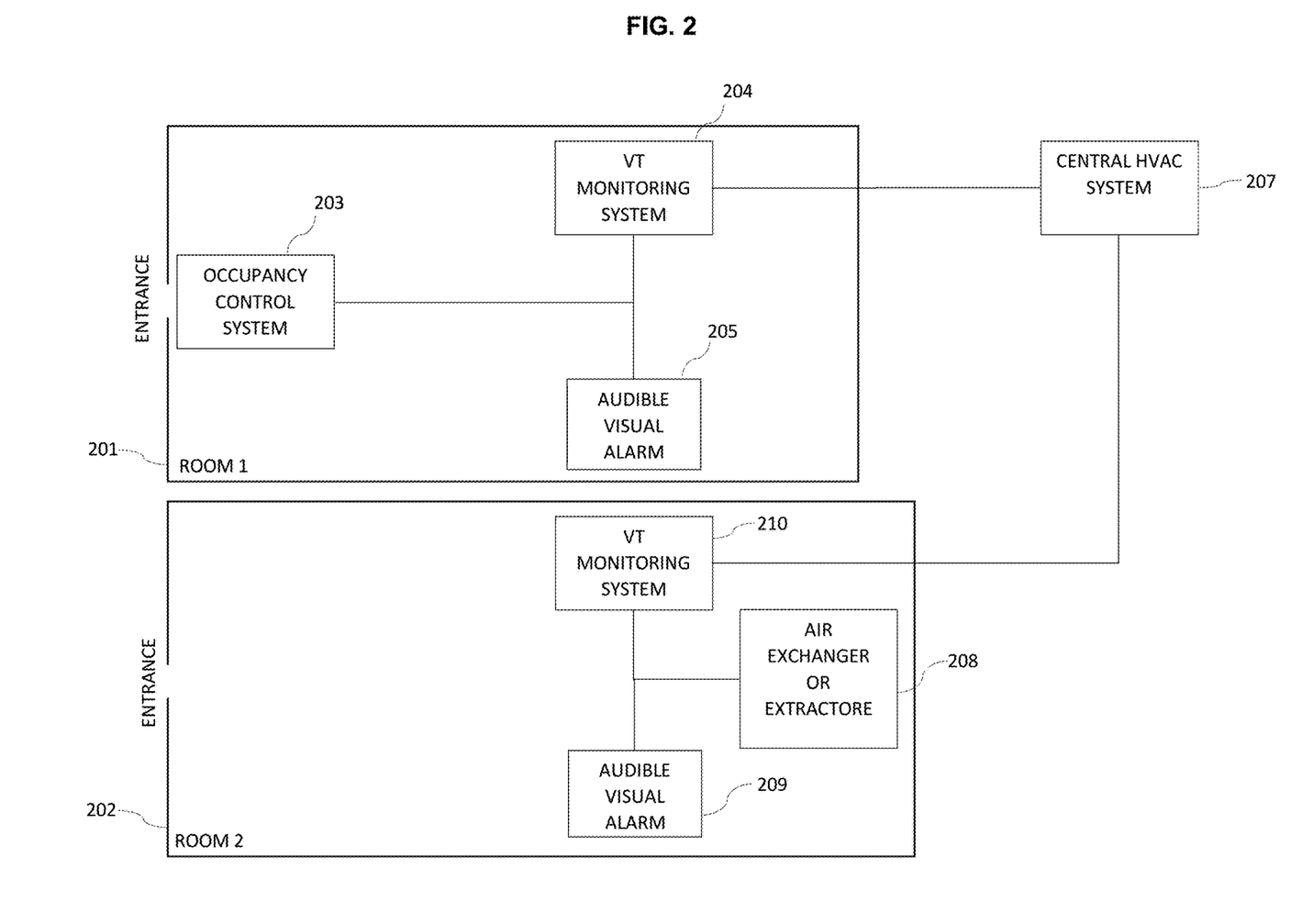
FIG. 2 shows a set of VT monitoring systems installed in two rooms.

A network of viral transmission monitoring system can be used to minimize occupant exposure to viral disease transmission in multiple rooms. For example, in the illustration of FIG. 2, Room 1, 201, is equipped with an occupancy control system 203 that would limit the number of occupants entering the room based on continuous monitoring provided by the Viral transmission system 204. By limiting the number of occupants in the room the system will be able to maintain an occupancy rate that would be within the air filtration and fresh air intake of the central HVAC system 207. Alternatively, the viral transmission monitoring system 210, in room 2, 202, can activate a local air exchanger or air extractor 208 to ensure minimal viral transmission. In both cases, a local visual and/or audible alarm 205, 209 may also be used to warn occupants if conditions can not be controlled through the described methods.

The Viral Transmission monitoring system can communicate with its various sub systems and other external systems using both wired and wireless communication technologies. For example, in FIG. 3, a viral transmission monitoring system 304 collects data from a set of remote sensors 301 using wireless communication such as Zigbee, Bluetooth, WIFI, or LORA. The system can then send commands to an HVAC controller such as a smart thermostat 305 using similar wireless technologies. This system may send data to the dedicated cloud solution 307, using WIFI, GPRS, or any other wireless communication. A second example is provided where a viral transmission monitoring system 303 communicates with a set of remote sensors 302 through a hard-wired connection. The data can be sent through a hardwired connection to the internet 306 or other networks. This connection can also be used to power the viral transmission monitoring system using POE or similar technology.

Figure 3:
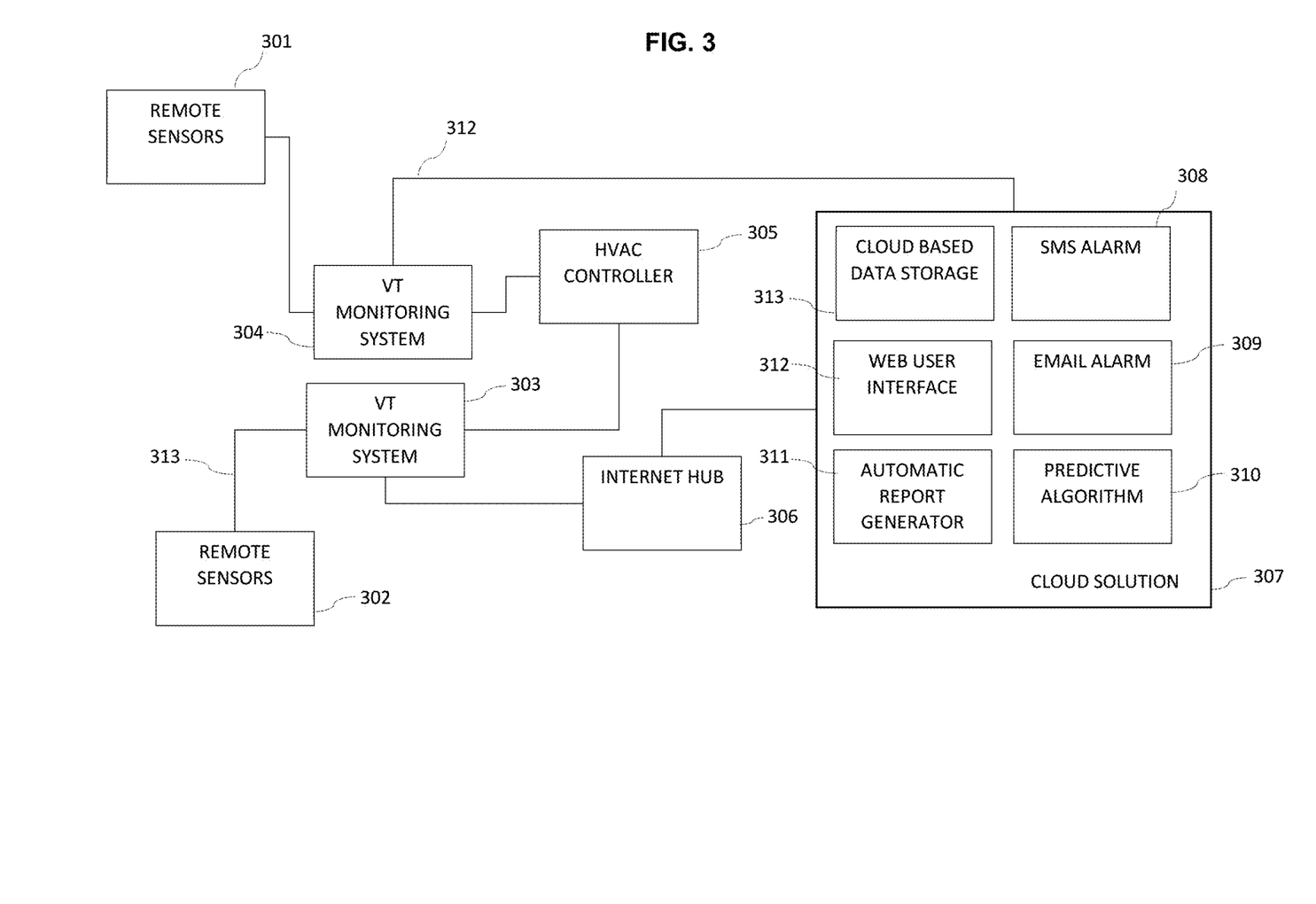
FIG. 3 shows a set of VT monitoring systems in communication with other systems.

The information transmitted may be stored in a cloud-based data storage server 313 where the user interface 312 would be used to retrieve the data from. The cloud solution may also include SMS alarm 308 and email alarm 309 notifications to inform appropriate personnel of any potentially hazardous conditions related to viral disease transmission. Automated reports 311 and condition predictions using predictive algorithms 310 may be generated from historic data collected to provide facility operators as a valuable tool in site assessment, improvements, and occupancy control procedures.

Figure 4:
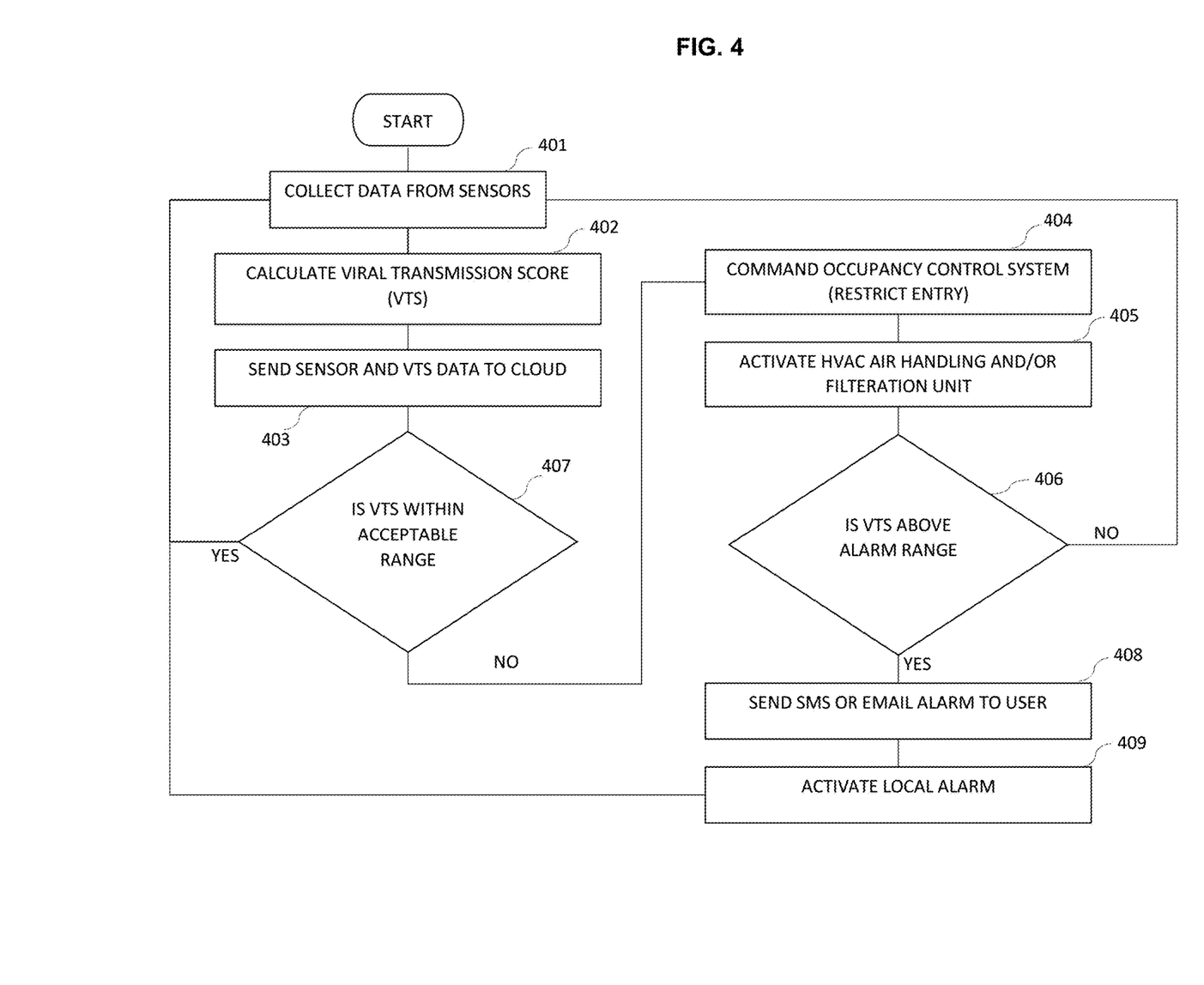
FIG. 4 shows a diagram for Viral Transmission Scoring system.

The Viral Transmission Scoring system starts by collecting data from all available sensors 401 as shown in FIG. 4. The data is used to generate a singular metric of viral transmission score (VTS) 402. Viral transmission score is related to the probability of viral disease transmission among occupants within the monitored space. This probability is calculated based on environmental parameters such as carbon dioxide concentration, fine particulate concentration, temperature, and relative humidity. It takes into consideration the combined effects of all the monitored parameters. For example, higher relative humidity hinders viral disease transmission by reducing the time the virus is airborne. Fine particulate may increase viral transmission probability as viruses may stay airborne longer by attaching to these particles. Carbon dioxide concentration can be used to determine ratio of occupancy loading to fresh air intake without direct measurement of each of these parameters.

The viral transmission score is then compared to a user defined limit to determine if the space has an acceptable probability of viral disease transmission 407. An occupancy control system 404, can be triggered to restrict further access to the monitored space. Air handling and filtration unit can be engaged 405 to reduce the viral transmission score with or without occupancy control based on feedback from the viral transmission monitoring system. If the viral transmission score is not controlled and exceeds hazardous levels 406, a local alarm 409 or remote alarm using SMS or email 408 can be triggered.

Viral Transmission Score (VTS)—VTS is designed to consider all factors that may increase or decrease the probability of viral transmission. First the occupancy level is determined using the occupancy sensors, which are translated into the CO2 concentration and the rate of change of CO2 concentration in time. A CO2 factor, $V_{CO_2}$ is determined that provides an indirect measurement of the occupancy load of the room vs the fresh air intake. It considers both the CO2 concentration as well as its rate of change. The CO2 concentration is scaled based on the maximum healthy concentration (for example 1000 ppm) and ambient CO2 concentration level. The ambient CO2 concentration can be acquired from external instruments or assumed to be 400 ppm to simplify the system. The rate of change is also scaled to the maximum safe rate of change (for example 0.75 ppm/min) and added to the scaled CO2 concentration to determine the total VCO2. The CO2 factor, $V_{CO_2}$, is defined as $$V_{CO_2} = 9 \left[ \frac{\min(CO2, K_{CO2}) - CO2_{ext}}{K_{CO2} - CO2_{ext}} + \frac{\min\left[\max\left(\frac{dCO_2}{dt}, 0\right), K_{dCO2}\right]}{K_{dCO2}} \right]$$

where $K_{CO2}$ and $K_{dCO2}$ have a set of predefined values. The preferred values for these parameters are $K_{CO2}=1000$, $K_{dCO2}=0.75$. Also, $CO2_{ext}$ is the CO2 concentration of the ambient air, which is measured by a sensor. For standard conditions, $$CO2_{ext} = 400. \frac{dCO_2}{dt}$$

is the rate of change of the concentration which is determined based on the time history of the CO2. The function $\min(CO2, K_{CO2})$ means the minimum values of the CO2 and $K_{CO2}$. And the function $$\min\left[\max\left(\frac{dCO_2}{dt}, 0\right), K_{dCO2}\right],$$

limits the value of the rate of change of CO2 between 0 and the constant $K_{dCO2}$.

Relative humidity is inversely corelated to the final viral transmission score and is used to amplify the VCO2 term. Airborne viruses are transmitted through water droplets or mucus from an infected individual. Dry air (lower relative humidity) dries up the water droplet faster reducing its weight and therefore allowing the virus to stay airborne longer. A relative humidity factor, $V_{RH}$ is defined as $$V_{RH} = 1 + K_{RH}\left(\frac{100 - RH}{100}\right)$$

where $K_{RH}$ is a predefined constant and is obtained to normalize the effect of the humidity in the viral transmission score. The preferred value for this constant is $K_{RH}=0.3$.

Fine particulate matter less than 2.5 microns in diameter, act as carriers and therefore increase the rate of viral transmission. Without particulate matter, a virus will stay airborne until it comes into contact with a stationary surface. The virus will then remain on the surface regardless of any air disturbance. However, a virus that has attached itself to dust or other particulate matter may settle on a stationary surface but will become again airborne if it is disturbed. A particulate matter factor, $V_{PM}$ is defined as $$V_{PM} = 1 + \left(\frac{PM_{2.5}}{K_{PM}}\right)$$

where $K_{PM}$ is a predefined constant and is obtained to normalize the effect of the particulate matter in the viral transmission score. Its values is obtained to be $K_{PM}=50$.

Viruses degrade at faster rate when the temperature increases. The temperature dependent term of the viral transmission score is used to suppress the probability of viral transmission if the temperature exceeds the pre-set limit. The rate of suppression increases as the temperature increases until it reaches a maximum suppression value. This term is virus dependent, for example, COVID-19 viruses start to decay at 30° C. and will completely degrade at 60° C. within minutes. The final Viral transmission score is calculated as a single number between 1 and 10 by multiplying all four (4) terms described above. A temperature factor, $V_T$, is defined as $$V_T = \min\left\{\max\left[1 - \left(\frac{1 - K_T}{K_{TL2} - K_{TL1}}\right)(T - K_{TL1}), K_T\right], 1\right\}$$

where T is the ambient temperature in Celsius, $K_T=0.5$, $K_{TL1}=30$, and $K_{TL2}=60$.

All the factors are combined and normalized in such a manner to provide a score between 1 and 10, or $VTS=V_{CO_2} \cdot V_{RH} \cdot V_{PM} \cdot V_T+1$. Therefore, the VTS equation is written as, $$VTS = \text{Min}(V_{CO_2} \cdot V_{RH} \cdot V_{PM} \cdot V_T + 1, 10)$$

which is the minimum value between 1 and 10. The Viral Transmission Score (VTS) equation is based on the premise that the probability of viral transmission is linearly related to the occupancy load of the space compared to the fresh air intake. Other factors such as humidity, temperature, and fine particulate can amplify or suppress this probability.

Consider the following example of a lecture hall where students enter after prolong inoccupancy with low fresh air intake. The rate of change of CO2 will be high and therefore the VTS score will be high. The VTS score will increase as the CO2 concentration increases with continual occupancy. After 1 hour of lecture the CO2 concentration is high, but the rate of change is low as the CO2 concentration has stabilized at a high value. The calculated VTS will remain high.

Directly after the lecture the rate of change will be negative, but CO2 concentration will still be high and therefore the VTS will correctly indicate the danger of continual airborne viruses and remain high. During lecture, the blackboard is erased creating a spike in fine particulate matter and VTS score. These particles will travel within the airspace and allow particulates to stay airborne until the particles are removed by means of filtration or fresh air exchange.

Figure 5A:
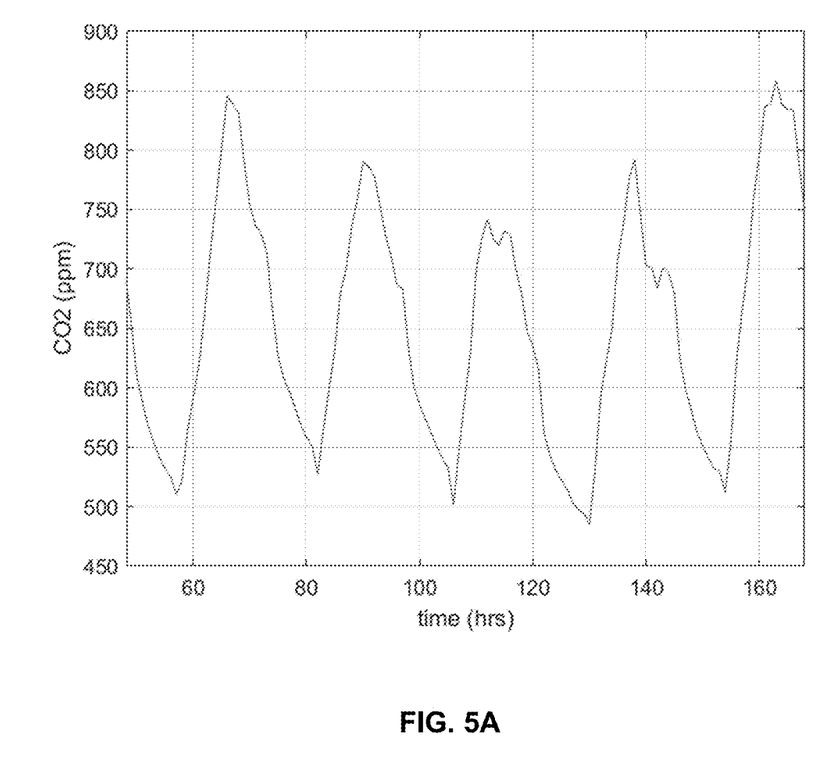
FIG. 5A shows the carbon dioxide sensor continuously measures the level of CO2 in the indoor space (at a pharmacy for 5 days)
Figure 5B:
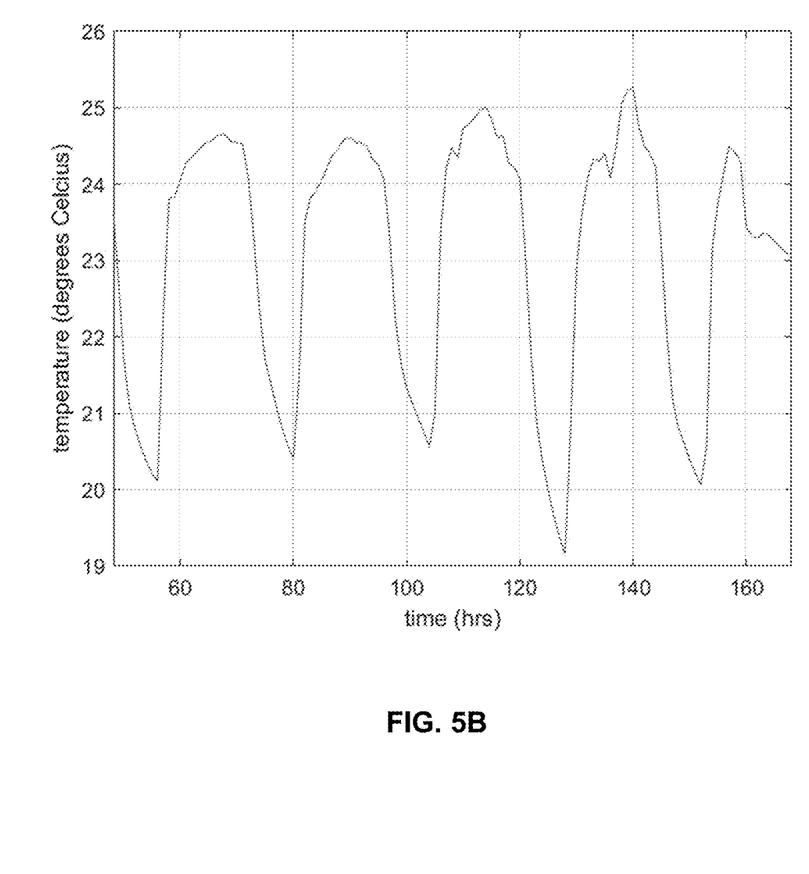
FIG. 5B shows the temperature variation in the space (at a pharmacy for 5 days)
Figure 5C:
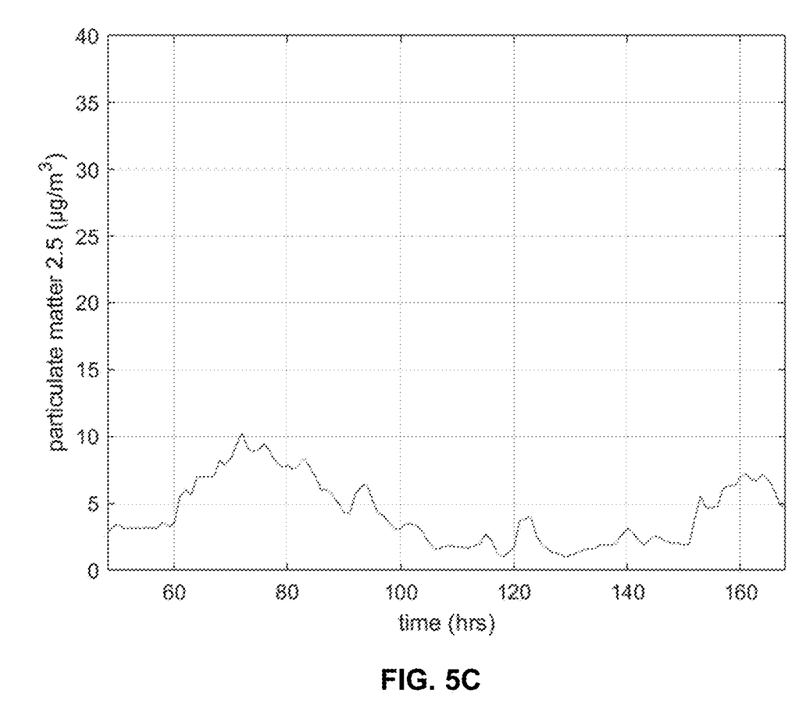
FIG. 5C shows the variation of the particulate matter in the space with time (at a pharmacy for 5 days)
Figure 5D:
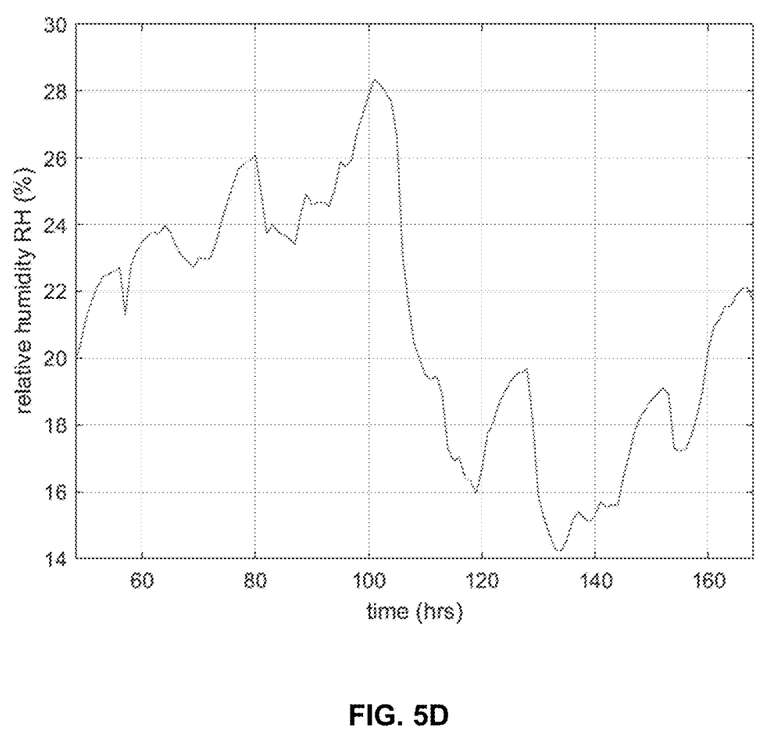
FIG. 5D shows the variation of the relative humidity in the space (at a pharmacy for 5 days)

FIGS. 5A-5E show an example of using the Viral Transmission Score at a pharmacy in Canada. As shown in FIG. 5A, the carbon dioxide sensor continuously measures the level of CO2 in the indoor space. In a 24-hour period, as people enter into the space, the level of CO2 increases, and towards the evening, as the people leave and the occupancy level goes down, the CO2 level reduces. This cyclic process is observed every 24 hours with some deviation due to the changes in the occupancy level. FIG. 5B shows the temperature variation in the space, which is also cyclic. The temperature is higher when there are more people and lower towards the evening. The ambient temperature can effect the indoor space temperate to some extent. FIG. 5C shows the variation of the particulate matter in the space with time, which is not cyclical. Small particles can linger in the air for a long time, resulting in the accumulation and increase in the PM concentration. Increase in the air filtration can help reduce the particulate matter concentration. FIG. 5D shows the variation of the relative humidity in the space, which also shows an accumulative behavior. The relative humidity has dropped when the air filtration rate is increased.

Figure 5E:
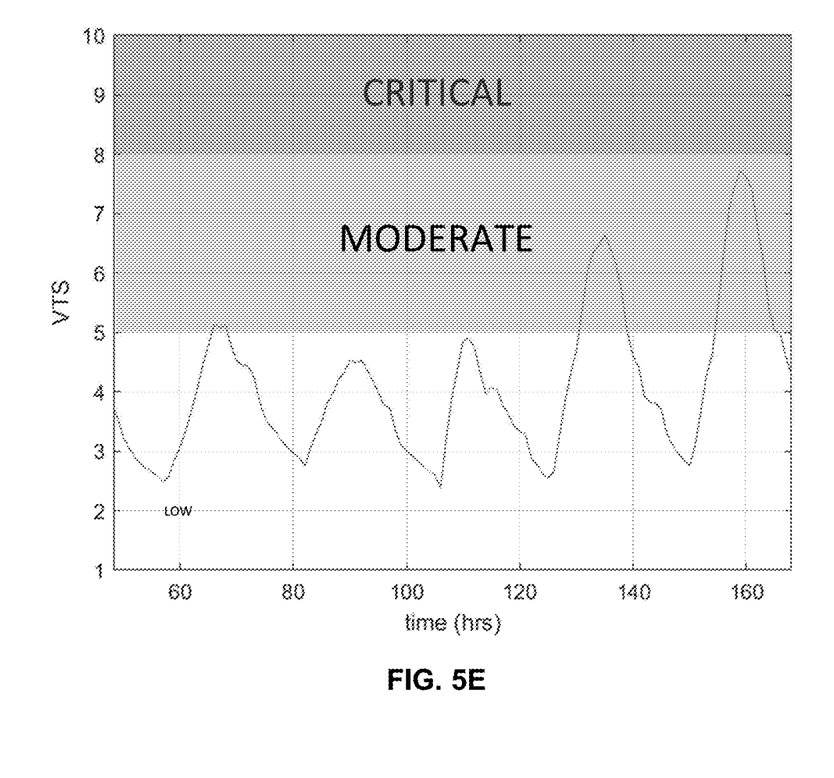
FIG. 5E shows the variation of the VTS with time for the space (at a pharmacy for 5 days).

FIG. 5E shows the variation of the VTS with time for the space, which is obtained by combining all the data gathered by all the sensors and using the method provided here to determine VTS. The VTS score shown in FIG. 5A is divided into three (3) ranges:
  Low probability with score of 1 to 5 shows ideal conditions and requires no action,
  Moderate probability spanning VTS of 5 to 7 indicating pro-active measures such as upgrade of HVAC system or reduction of occupancy loading is required. Systems with intelligent HVAC or air filtration systems would activate at higher capacity when VTS reaches this range.
  Critical range of 7 to 10 indicating immediate action is required including reduction of occupancy load.

The results demonstrate the importance of the interaction of all measured parameters. For example, while occupancy loading had not increased between 130-170 hours as demonstrated by the CO2 measurements, the VTS score shows exceedance into the Moderate range due to low humidity levels. This information could be used by the facility manager to improve humidification of the space to ensure a safer environment for the occupants.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A system for assessing an air quality of an indoor space for viral particle transmission, comprising:
  a) a Carbon dioxide sensor placed inside the indoor space to continuously measure a CO2 concentration of the indoor space, CO2;
  b) a relative humidity sensor to measure a relative humidity of the indoor space, RH;
  c) a particulate matter sensor to measure particle counts of the indoor space preferably particles of less than 2.5 micron, $PM_{2.5}$;
  d) a temperature sensor to measure a temperature of the indoor space, T;
  e) a processor configured to determine:
    a rate of change of Carbon dioxide concentration in the indoor space, $$\frac{dCO_2}{dt},$$

and determine a Carbon dioxide parameter, $V_{CO_2}$ by formula:

$$V_{CO_2} = 9\left[\frac{\min(CO2, K_{CO2}) - CO2_{ext}}{K_{CO2} - CO2_{ext}} + \frac{\min\left[\max\left(\frac{dCO_2}{dt}, 0\right), K_{dCO2}\right]}{K_{dCO2}}\right]$$

wherein $K_{CO2}$ and $K_{dCO2}$ have a set of predefined values or $K_{CO2}$=1000, $K_{dCO2}$=0.75, and $CO2_{ext}$ is the CO2 concentration of the ambient air that is measured directly or set equal to 400;
    a relative humidity factor, $V_{RH}$, by formula:

$$V_{RH} = 1 + 0.3\left(\frac{100 - RH}{100}\right)$$

a particulate matter factor, $V_{PM}$, by formula:

$$V_{PM} = 1 + \left(\frac{PM_{2.5}}{50}\right)$$

a temperature factor, $V_T$, by formula:

$$V_T = \min\left\{\max\left[1 - \left(\frac{1 - K_T}{K_{TL2} - K_{TL1}}\right)(T - K_{TL1}), K_T\right], 1\right\}$$

wherein $K_T$, $K_{TL1}$, and $K_{TL2}$ are a set of predetermined parameters or are $K_T$=0.5, $K_{TL1}$=30, and $K_{TL2}$=60;
    a Viral Transmission Score, VTS, for the indoor space by formula:

$$VTS = V_{CO_2} \cdot V_{RH} \cdot V_{PM} \cdot V_T + 1$$

whereby higher values of VTS represent higher probability of viral transmission in the indoor space.

2. The system of claim 1, further having an alarm system to alarm or having a notification system to send notification to facility operators, if the VTS reaches the predefined value.

3. The system of claim 1, wherein the processor is configured to provide information to an HVAC control system to increase an air flow rate or an air filtration rate of the HVAC system to reduce the VTS.

4. A system for assessing an air quality of an indoor space for viral particle transmission, comprising:
  a) a Carbon dioxide sensor placed inside the indoor space to continuously measure a CO2 concentration of the indoor space, CO2;
  b) a processor configured to continuously receive CO2 concentration of the indoor space, CO2, and determine a rate of change of Carbon dioxide concentration in the indoor space, $$\frac{dCO_2}{dt},$$

and determine a Carbon dioxide parameter, $V_{CO_2}$, by formula:

$$V_{CO_2} = 9\left[\frac{\min(CO2, K_{CO2}) - CO2_{ext}}{K_{CO2} - CO2_{ext}} + \frac{\min\left[\max\left(\frac{dCO_2}{dt}, 0\right), K_{dCO2}\right]}{K_{dCO2}}\right]$$

wherein $K_{co2}$ and $K_{dco2}$ have a set of predefined values or $K_{co2}=1000$, $K_{dCO2}=0.75$, and $CO2_{ext}$ is the CO2 concentration of the ambient air, and calculate a Viral Transmission Score, VTS, for the indoor space by formula:

$$VTS = V_{CO_2} + 1$$

whereby higher values of VTS represent higher probability of viral transmission in the indoor space.

5. The system of claim 4, further having a relative humidity sensor to measure a relative humidity of the indoor space, RH, and wherein the processor is configured to further determine a relative humidity factor, $V_{RH}$, by formula:

$$V_{RH} = 1 + 0.3\left(\frac{100 - RH}{100}\right)$$

and calculate VTS for the indoor space by formula:

$$VTS = V_{CO_2} \cdot V_{RH} + 1.$$

6. The system of claim 5, further having a particulate matter sensor to measure particle counts of the indoor space preferably for particles of less than 2.5 micron, $PM_{2.5}$, and wherein the processor is configured to further determine a particulate matter factor, $V_{PM}$, by formula:

$$V_{PM} = 1 + \left(\frac{PM_{2.5}}{50}\right)$$

and calculate VTS for the indoor space by formula:

$$VTS = V_{CO_2} \cdot V_{RH} \cdot V_{PM} + 1.$$

7. The system of claim 6, further having a temperature sensor to measure a temperature of the indoor space, T, and wherein the processor is configured to further determine a temperature factor, $V_T$, by formula:

$$V_T = \min\left\{\max\left[1 - \left(\frac{1 - K_T}{K_{TL2} - K_{TL1}}\right)(T - K_{TL1}), K_T\right], 1\right\}$$

wherein $K_T$, $K_{TL1}$, and $K_{TL2}$ are a set of predetermined parameters or are $K_T=0.5$, $K_{TL1}=30$, and $K_{TL2}=60$, and calculate VTS for the indoor space by formula:

$$VTS = V_{CO_2} \cdot V_{RH} \cdot V_{PM} + 1.$$

8. A method for assessing an air quality of an indoor space for viral particle transmission, comprising the steps of:

measuring a CO2 concentration of the space and the ambient outside of the space, and determining a rate of change of CO2 concentration of the space, and calculating a CO2 factor, $V_{CO_2}$ by formula:

$$V_{CO_2} = 9\left[\frac{\min(CO2, K_{CO2}) - CO2_{ext}}{K_{CO2} - CO2_{ext}} + \frac{\min\left[\max\left(\frac{dCO_2}{dt}, 0\right), K_{dCO2}\right]}{K_{dCO2}}\right]$$

wherein $K_{cO2}$ and $K_{dcO2}$ have a set of predefined values or $K_{co2}=1000$, $K_{dcO2}=0.75$, and $CO2_{ext}$ is the CO2 concentration of the ambient air that is either measured or set equal to 400;

measuring a relative humidity of the space and calculating a relative humidity factor, $V_{RH}$, by formula:

$$V_{RH} = 1 + 0.3\left(\frac{100 - RH}{100}\right)$$

measuring a particulate matter concentration of the space and calculating a particulate matter factor, $V_{PM}$, by formula:

$$V_{PM} = 1 + \left(\frac{PM_{2.5}}{50}\right)$$

measuring a temperature of the space and calculating a temperature factor, $V_T$, by formula:

$$V_T = \min\left\{\max\left[1 - \left(\frac{1 - K_T}{K_{TL2} - K_{TL1}}\right)(T - K_{TL1}), K_T\right], 1\right\}$$

wherein $K_T=0.5$, $K_{TL1}=30$, and $K_{LT2}=60$, and calculating a Viral Transmission Score (VTS) as a single number by formula:

$$VTS = V_{CO_2} \cdot V_{RH} \cdot V_{PM} + 1.$$

whereby the VTS represents a probability of viral transmission that is configured to provide a higher score for spaces with higher occupancy to fresh air intake ratio; a higher score for spaces with possible accumulated viral load from prior occupancy; a higher score for spaces with higher particulate count; a higher score for spaces with particulate distribution favoring smaller particulate sizes; a higher score for spaces with lower relative humidity, and a lower score for spaces with temperature above virus tolerance.

* * * * *